(12) United States Patent
Boedecker et al.

(10) Patent No.: US 9,538,958 B2
(45) Date of Patent: Jan. 10, 2017

(54) PERMITTIVITY SHIELDING

(71) Applicant: Vital Sensors Holding Company, Inc., Chicago, IL (US)

(72) Inventors: Volker Boedecker, Hannover (DE); Axel Niemeyer, Bielefeld (DE); Bernhard Wagner, Wunstorf (DE)

(73) Assignee: ENDOTRONIX, INC., Woodridge, IL (US)

( * ) Notice: Subject to any disclaimer, the term of this patent is extended or adjusted under 35 U.S.C. 154(b) by 0 days.

(21) Appl. No.: 14/385,691

(22) PCT Filed: Mar. 14, 2013

(86) PCT No.: PCT/US2013/031505
§ 371 (c)(1),
(2) Date: Sep. 16, 2014

(87) PCT Pub. No.: WO2013/138624
PCT Pub. Date: Sep. 19, 2013

(65) Prior Publication Data
US 2015/0374295 A1    Dec. 31, 2015

Related U.S. Application Data

(63) Continuation of application No. 13/422,216, filed on Mar. 16, 2012, now abandoned.

(51) Int. Cl.
| | |
|---|---|
| *A61B 5/02* | (2006.01) |
| *A61B 5/00* | (2006.01) |
| *A61B 5/0215* | (2006.01) |
| *G01L 11/02* | (2006.01) |
| *A61B 5/021* | (2006.01) |

(52) U.S. Cl.
CPC .......... *A61B 5/6876* (2013.01); *A61B 5/0215* (2013.01); *G01L 11/025* (2013.01); *A61B 5/021* (2013.01); *A61B 2562/028* (2013.01); *A61B 2562/0214* (2013.01); *A61B 2562/0247* (2013.01); *A61B 2562/125* (2013.01); *A61B 2562/182* (2013.01); *A61M 2205/3331* (2013.01)

(58) Field of Classification Search
CPC ............ A61B 2562/0247; A61B 5/021; A61M 2205/3331
See application file for complete search history.

(56) References Cited

U.S. PATENT DOCUMENTS

| | | |
|---|---|---|
| 6,919,101 B2 | 7/2005 | Zhang et al. |
| 6,958,509 B2 | 10/2005 | Korner et al. |
| 7,682,313 B2 | 3/2010 | Bodecker et al. |
| 7,686,768 B2 | 3/2010 | Bodecker et al. |
| 7,931,597 B2 | 4/2011 | Bodecker et al. |
| 7,931,598 B2 | 4/2011 | Bodecker et al. |

(Continued)

FOREIGN PATENT DOCUMENTS

| | | |
|---|---|---|
| CN | 1437268 A | 8/2003 |
| CN | 102169037 A | 8/2011 |

(Continued)

OTHER PUBLICATIONS

International Search Report and Written Opinion for PCT/US2013/031505, dated Jun. 27, 1013.

*Primary Examiner* — Jacqueline Cheng
*Assistant Examiner* — Puya Agahi
(74) *Attorney, Agent, or Firm* — McDonald Hopkins LLC

(57) ABSTRACT

Techniques for shielding permittivity-sensitive devices are disclosed.

20 Claims, 4 Drawing Sheets

(56) References Cited

U.S. PATENT DOCUMENTS

| | | |
|---|---|---|
| 8,161,811 B2 | 4/2012 | Beck et al. |
| 8,380,273 B2 | 2/2013 | Say et al. |
| 2001/0029331 A1 | 10/2001 | Ginggen et al. |
| 2002/0045921 A1 | 4/2002 | Wolinsky et al. |
| 2003/0040161 A1 | 2/2003 | Schrenk et al. |
| 2003/0187338 A1 | 10/2003 | Say et al. |
| 2005/0234316 A1 | 10/2005 | Colvin et al. |
| 2008/0103064 A1 | 5/2008 | Labgold |
| 2008/0150066 A1 | 6/2008 | Lee |
| 2010/0013036 A1 | 1/2010 | Carey |
| 2010/0145183 A1 | 6/2010 | Wahlstrand et al. |
| 2010/0145422 A1 | 6/2010 | Seymour et al. |
| 2010/0298679 A1 | 11/2010 | Wu et al. |
| 2010/0312081 A1 | 12/2010 | Benaron et al. |
| 2011/0201948 A1 | 8/2011 | Bodecker et al. |
| 2011/0201949 A1 | 8/2011 | Bodecker et al. |
| 2012/0175714 A1 | 7/2012 | Lakamraju et al. |

FOREIGN PATENT DOCUMENTS

| | | |
|---|---|---|
| JP | S6031032 A | 2/1985 |
| WO | WO-2006111877 A1 | 10/2006 |
| WO | WO-2010008383 A1 | 1/2010 |

PERMITTIVITY SHIELDING

CROSS-REFERENCE TO RELATED APPLICATIONS

This application claims priority to U.S. patent application Ser. No. 13/422,216 filed Mar. 16, 2012, which is hereby incorporated herein by reference in its entirety.

SUMMARY

Techniques for shielding permittivity-sensitive devices, for example in combination with a pressure-transferring and biocompatible material, are disclosed.

DETAILED DESCRIPTION

Figure 1:
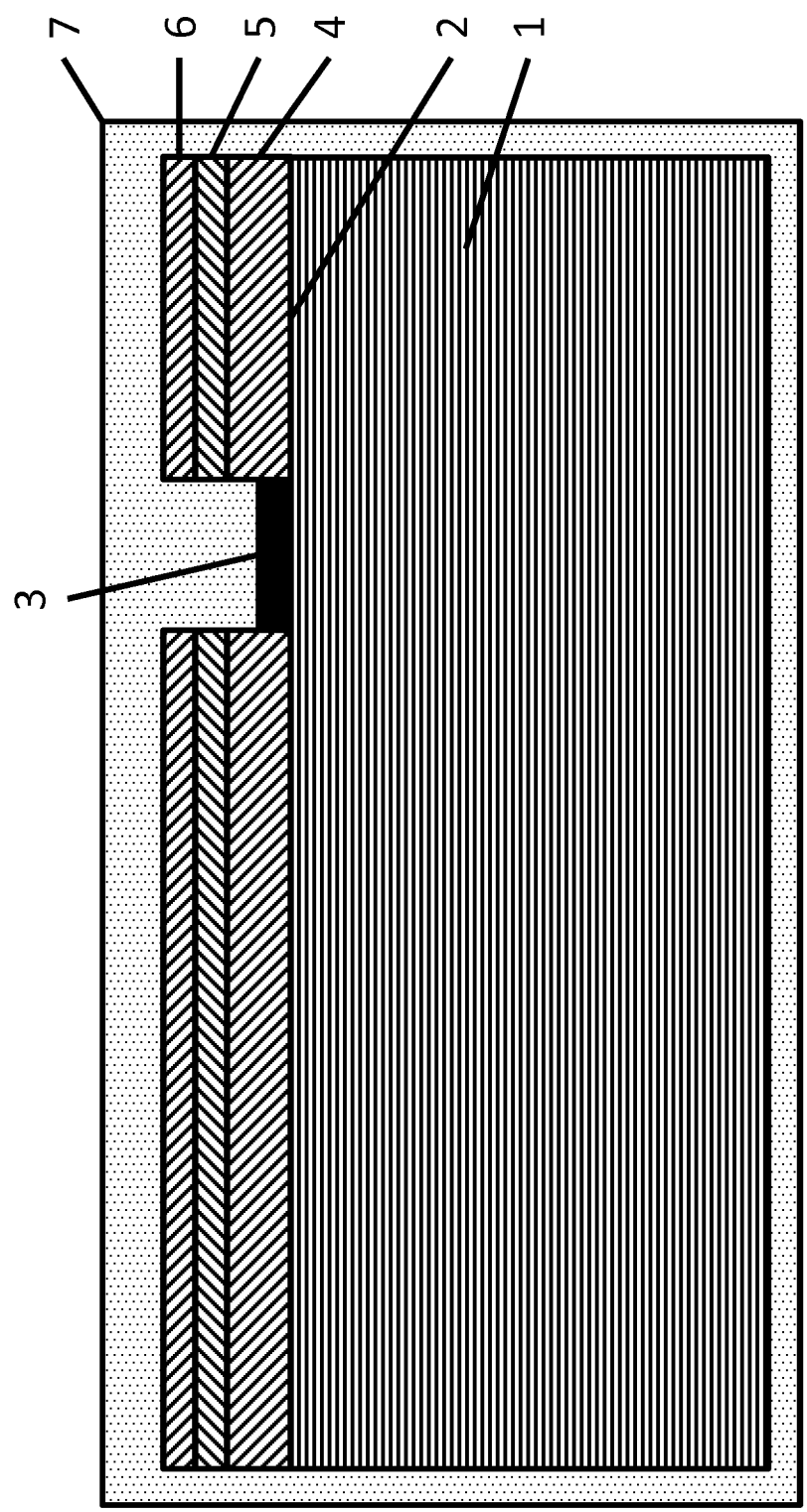
FIG. 1 shows a first embodiment of a bioimplantable sensor device with permittivity shielding.

The performance of solid state devices can be affected by changes in the electrical permittivity of the device's surroundings. Output from such a device can be misleading if the device was calibrated in one environment, e.g., air having a relative permittivity of roughly 1, and then operated in a different environment, e.g., liquid water which can have a relative permittivity around 80. (The relative permittivity of water is highly variable as a function of temperature, frequency, salinity, etc.) The effect of a changing permittivity environment could be important in a wide variety of applications of permittivity-sensitive devices, and in particular it has been observed in the in vivo use of capacitive pressure sensors.

Capacitive pressure sensors are sometimes used in situations where recalibration is difficult, e.g., in vivo uses for measuring blood pressure, and inside automobile tires for measuring tire air pressure. In such contexts, it would be useful to avoid having to recalibrate a sensor to account for changes in the permittivity environment. Permittivity shielding can minimize the effect of a changing permittivity environment on a solid state device, reducing or eliminating the need for recalibration.

Any device that is sensitive to changes in the permittivity of its environment could potentially benefit from permittivity shielding. Semiconductor devices, for example complementary metal-oxide semiconductor (CMOS) devices, are known under certain circumstances to be sensitive to changes in environmental permittivity. Microelectromechanical systems (MEMS) may also be sensitive to changes in environmental permittivity. Such MEMS may be designed to act as sensors, including capacitive pressure sensors, and may be formed on a CMOS semiconductor device.

MEMS capacitive pressure sensors can be used in a variety of contexts to measure the pressure of a fluid, for example measuring blood pressure or measuring air pressure inside a tire. In order to measure blood pressure, the capacitive pressure sensor will typically be rendered biocompatible, for example, by encapsulating the device in a biocompatible material such as silicone. Silicone fulfills the technical and biological requirements that are needed for a long-term implant for measuring pressure. Silicone is a nearly ideal material because of its biocompatibility, long-term stability, and ability to transfer pressure from its inner surface to its outer surface.

But silicone is biocompatible in part because it is porous. When silicone is exposed to a fluid, such as blood, fluid and/or vapor will infiltrate the silicone. This infiltration will displace air, or whatever fluid was present prior to submersion, changing the permittivity of the surroundings, and thereby acutely changing the capacitive pressure sensor readings. Recalibration is therefore required immediately after immersion. Moreover, the process of infiltration may take a widely varying amount of time such that capacitive pressure sensor readings may continue to change over hours, days or even weeks. And because the composition of the infiltrating substance can change over time (for example as blood chemistry, concentration of medications, and other health conditions vary) the effect of infiltration on permittivity may vary unpredictably. This unpredictability requires that the calibration of the sensor be vigilantly monitored over long periods of time. Different protective coatings, typically plastics or other non-metals, may be preferred for other applications, but alternative coatings that are similarly porous will have many of the same advantages and disadvantages as silicone.

FIG. 1 shows one embodiment of a bioimplantable sensor device. In this embodiment, the bioimplantable sensor device includes a semiconductor device 1 having an exterior surface 2. A sensor 3 is formed on the exterior surface 2 of the semiconductor device 1. A first layer of metallic adhesive 4 is adhered to a portion of the exterior surface 2 of the semiconductor device 1. A layer of permittivity shielding 5 overlies and is adhered to the first layer of metallic adhesive 4 in order to improve contact between the permittivity shield and the semiconductor device 1. A second layer of metallic adhesive 6 overlies and is adhered to the layer of permittivity shielding 5. A biocompatible, outermost protective layer 7 overlies and is adhered to the second layer of metallic adhesive 6 in order to improve contact between the permittivity shielding 5 and the protective layer 7. Strong adhesion between these layers prevents local delamination of the protective layer 7 (typically silicone in biological applications), the resultant change in its mechanical properties of the embedding silicone layer, and the consequent changes in the calibration parameters (i.e., change of the pressure transfer function). Although FIG. 1 shows the first layer of metallic adhesive 4 directly contacting the exterior surface 2, it will be understood that the electronic elements of the semiconductor device will be electrically isolated from any metal applied to the exterior. Typically the layer of permittivity shielding 5 will be electrically connected to ground. Alternatively, the permittivity shielding may be applied to just one surface of the semiconductor device 1, as shown in FIG. 1, or can overlie more than one side, or even all sides of the semiconductor device 1.

Typically, as shown in FIG. 1, the outermost protective layer 7 will fully encapsulate the semiconductor device 1. The metallic adhesives 4, 6 and permittivity shielding 5 will typically cover the entire exterior surface 2 of the device 1 except for that part of the surface on which the sensor 3 is formed, but alternatively may cover the sensor 3. Leaving the sensor 3 uncovered by the metallic adhesives 4, 6 and permittivity shielding 5 can improve the kinetic transmission of force to the sensor, which is particularly important if the sensor 3 is a capacitive pressure sensor.

Figure 2:
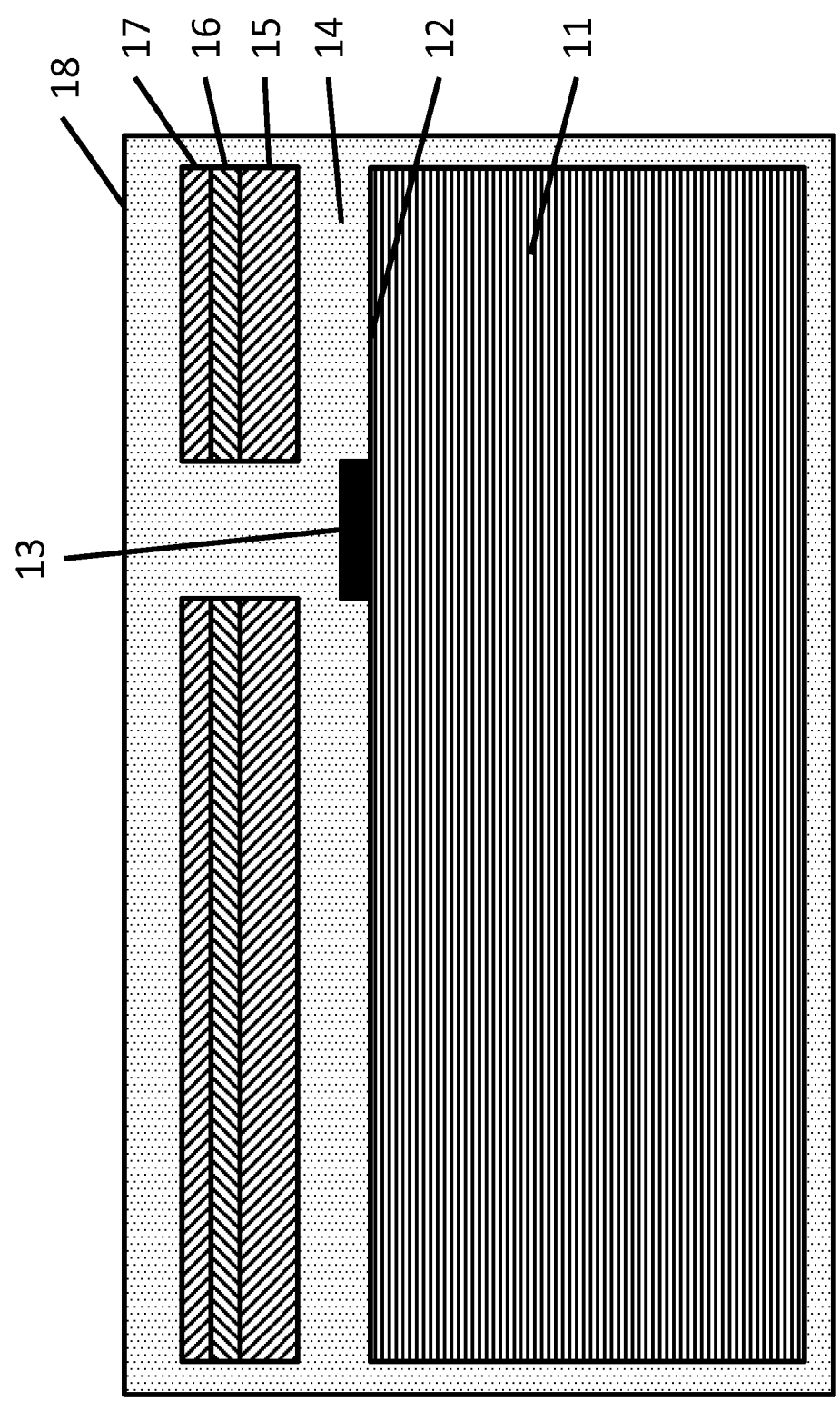
FIG. 2 shows a second embodiment of a bioimplantable sensor device with permittivity shielding.

FIG. 2 shows another embodiment of an implantable, biocompatible sensor device. In this embodiment, a first biocompatible protective layer 14 overlies and is adhered to a portion of the exterior surface 12 of the semiconductor device 11. Again, a sensor 13 is formed on the exterior surface 12. A first layer of metallic adhesive 15 overlies and is adhered to the first biocompatible protective layer 14. A layer of permittivity shielding 16 overlies and is adhered to the first layer of metallic adhesive 15. A second layer of metallic adhesive 17 overlies and is adhered to the layer of permittivity shielding 16. A second biocompatible, outermost protective layer 18 overlies and is adhered to the second layer of metallic adhesive 17. As with the embodiment of FIG. 1, the metallic adhesives 15, 17 and permittivity shielding 16 will typically cover the entire exterior surface 12 of the device 11 except for that part of the surface on which the sensor 13 is formed, but alternatively may cover the sensor 13.

Figure 3:
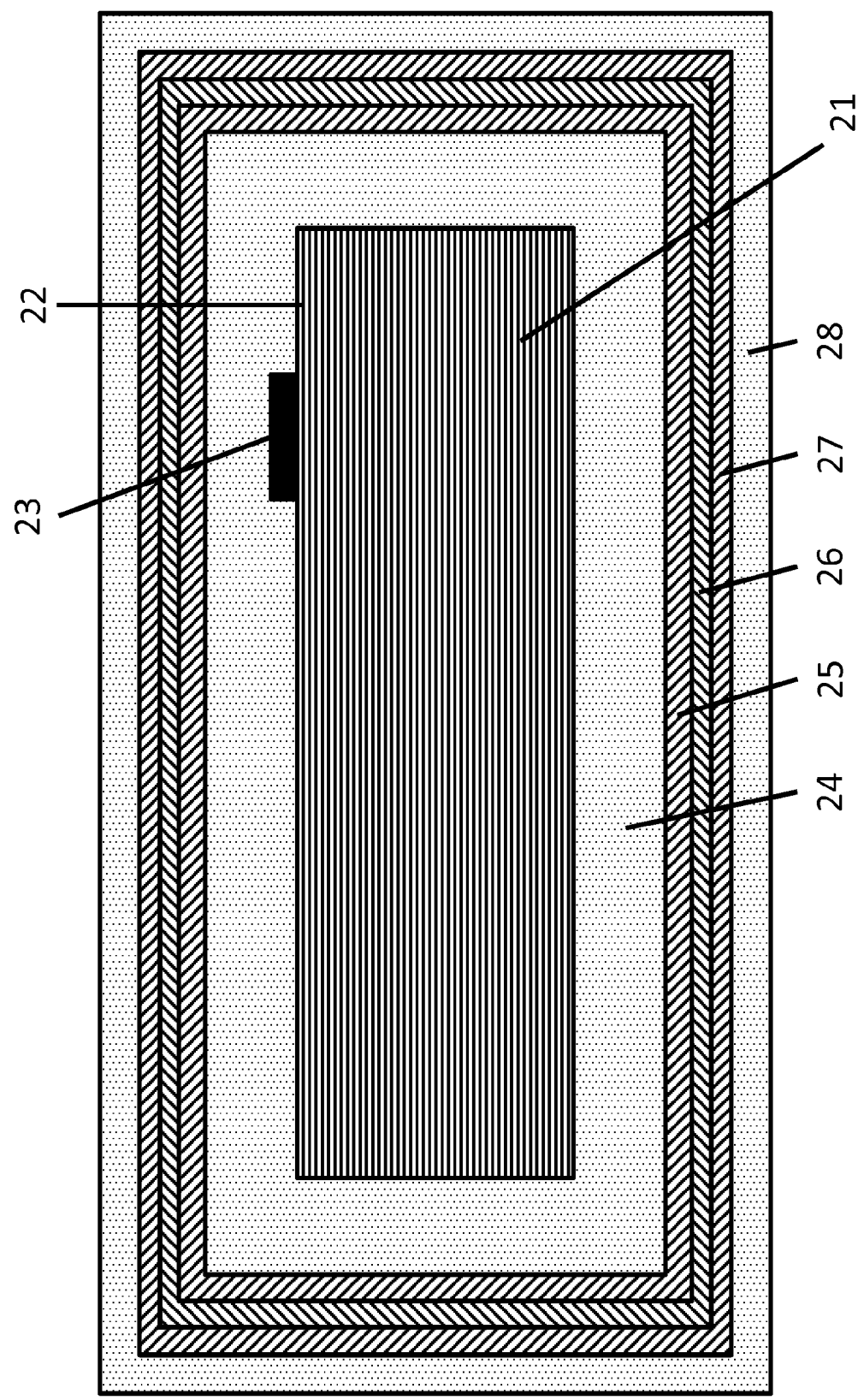
FIG. 3 shows a third embodiment of a bioimplantable sensor device with permittivity shielding.

FIG. 3 shows another embodiment of an implantable, biocompatible sensor device, having a semiconductor device 21 with an exterior surface 22, a sensor 23 formed thereon, a first biocompatible protective layer 24 overlying and adhered to a portion of the exterior surface 22 of the semiconductor device 21, a first layer of metallic adhesive 25 overlying is adhered to the first biocompatible protective and pressure-transferring layer 24, a layer of permittivity shielding 26 overlying and adhered to the first layer of metallic adhesive 25, a second layer of metallic adhesive 27 overlying and adhered to the layer of permittivity shielding 26, and a second biocompatible, outermost protective layer 28 overlying and adhered to the second layer of metallic adhesive 27. This embodiment is similar to the embodiment of FIG. 2, but differs in that the permittivity shielding 26, metallic adhesives 25 and 27, and outermost protective and pressure-transferring layer 28 each completely encapsulate the layers within. The permittivity shielding 26 and metallic adhesives 25 and 27 also overlie the sensor 23.

The sensor can be a microelectromechanical device formed on the surface of the semiconductor. The semiconductor can be a CMOS device. The sensor could be, for example, a capacitive pressure sensor.

The first and second layers of metallic adhesive may be the same material. The material may include, or consist substantially of or entirely of, an alloy of tungsten and titanium. The layer of permittivity shielding may include a conductive metal or metal alloy. The permittivity shielding may include, consist substantially of, or consist entirely of gold. The protective layer may include, consist substantially of, or consist entirely of silicone.

Either the metallic adhesive, or the permittivity shielding, or both, may be deposited by galvanic metallization, or sputtering, or any other process in which a thin layer of metal or metal alloy is deposited in a defined, predetermined geometry.

The permittivity shielding serves at least two purposes. First, a conductive (preferably highly conductive) permittivity shielding will help minimize the effect on the sensor of changes in permittivity in the neighborhood of the sensor. The conductive permittivity shielding can act as a partial Faraday cage, reducing the effect that changes in the permittivity environment have on electromagnetic fields in or around the sensor. The shielding effect also protects the whole electronic circuit implemented within the device.

Second, the permittivity shielding can act as a fluid barrier, preventing permittivity altering substances (e.g., blood) from permeating at least part of the protective layer. A thickness of roughly 0.2 to 5 microns is thought to be sufficient to render a layer of metallic permittivity shielding substantially water impermeable, but greater or lesser thicknesses may be required to make the barrier impermeable to other fluids. By isolating a protective layer from fluids, the fluid-impermeable permittivity barrier creates a zone around the sensor in which the permittivity environment is maintained and not altered. Furthermore, it may be advantageous that not only the area directly around the sensor but the whole electronic circuit should be protected against changing permittivity, because changing permittivity could also cause changes in the electronic circuit and therefore could result in changing the calibration data of the device. The fluid-free zone of the protective layer could be 0.3 to 2 millimeters thick, depending on the permittivity characteristics of the fluid in question.

In embodiments in which the permittivity shielding overlies the sensor, the sensor will work best if the permittivity shielding reliably and accurately transfers pressure. To achieve good pressure transfer the permittivity shielding, and associated adhesive layers, should be flexible. Thinner permittivity shielding is generally more flexible. But, as explained below, the permittivity shielding should also be fluid impermeable, which requires a certain minimum thickness that depends on the particular combination of fluid and shielding material. Gold has been found to work well, being relatively impermeable to blood and its constituents while still relatively thin and flexible. Gold also has the advantage that it is highly electrically conductive.

Figure 4:
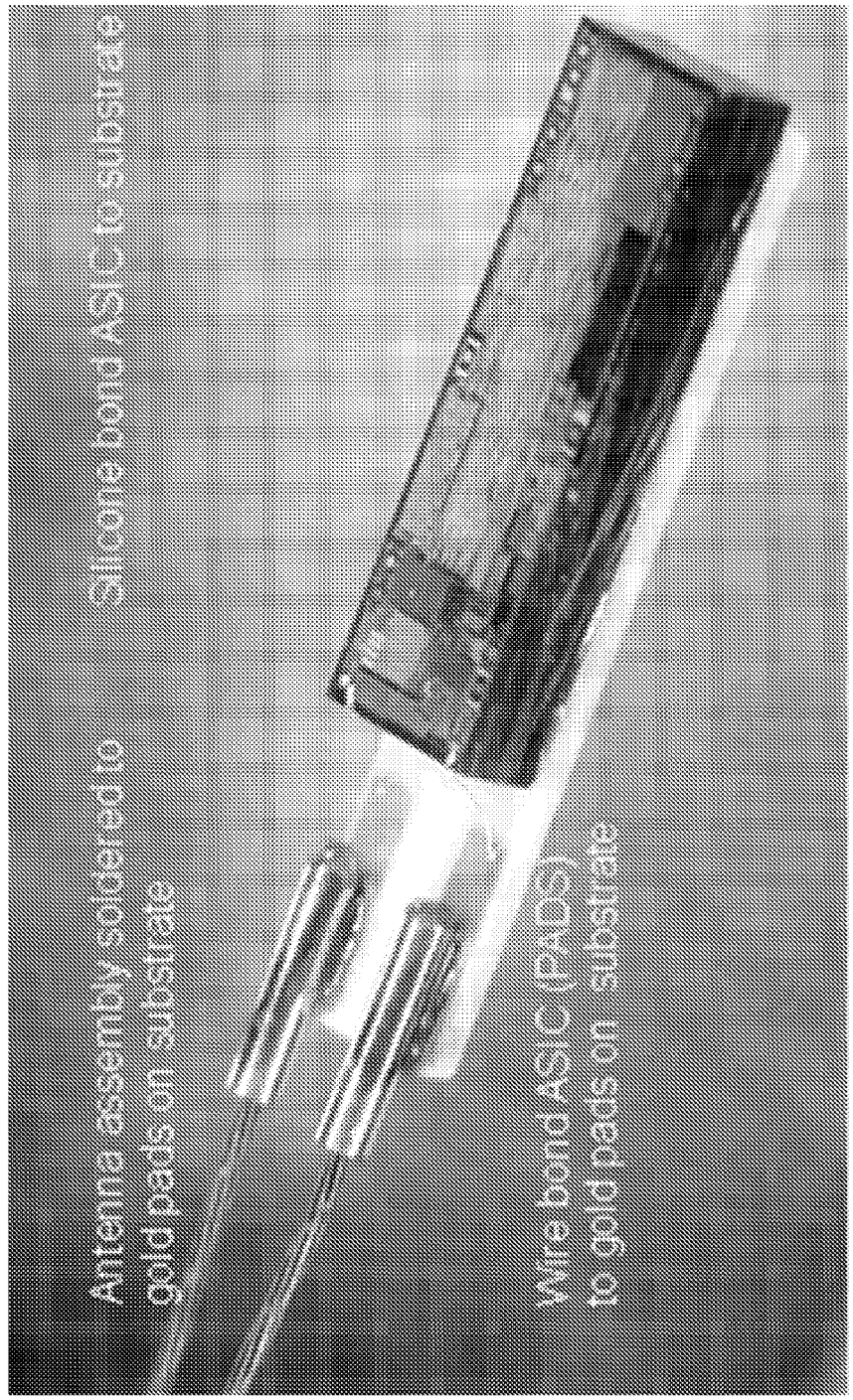
FIG. 4 is a photograph of a capacitive pressure sensor assembly.

The permittivity shielding described herein can be applied to a wide variety of systems, especially the implantable pressure monitors described in U.S. Pat. Nos. 7,682,313, 7,686,768, which are hereby incorporated herein by reference. One example of such an implantable pressure monitor is shown in FIG. 4, with an ASIC mounted on a substrate platform and connected by wires to an antenna assembly. Typically the entire device, including the substrate and other appendages such as antennae and connecting wires, will be encapsulated as shown in FIGS. 1-3. Such monitors can be implanted in positions to monitor a variety of cardiovascular spaces inside a patient, such as left atrium, right atrium, left ventricle, right ventricle, ascending aorta, aortic arch, descending thoracic aorta, abdominal aorta, pulmonary artery, brachiocephalic artery, right subclavian artery, left subclavian artery, right common carotid artery, left common carotid artery, left iliac artery, right iliac artery, right femoral artery, left femoral artery, etc.

In addition to the in vivo applications described above, sensors, particularly capacitive pressure sensors, can be employed in a wide variety of contexts. Permittivity shielding can be used and may be beneficial in any context where the permittivity environment may evolve over time and the performance of the sensor is susceptible to such changes. Of course, in non-biological contexts the protective layer need not be biocompatible, but may still be porous or otherwise susceptible to changes in permittivity, and therefore may benefit from the addition of permittivity shielding.

In capacitive pressure sensing, it is possible to correct for the effect of a changing permittivity environment even where no permittivity shielding is used. A capacitive pressure sensor is typically formed with active capacitive membranes that are sensitive to changes in pressure. The output signal from the active capacitive membranes is typically used to directly calculate the sensed pressure. But that output signal may partly be due to the impinging pressure and partly due to the permittivity environment. To deal with this problem, one can form the capacitive pressure sensor so that it also has passive capacitive membranes that are insensitive to changes in pressure. The signal from the passive capacitive membranes can then be interpreted as responding only to changes in permittivity. The signal due to permittivity can then be subtracted from the signal from the active capacitive membranes, leaving only signal due to changes in pressure. In this way, paired active and passive pressure membranes can be used to correct for changing permittivity.

We claim:

1. A bioimplantable sensor device shielded against changing permittivity comprising:
    a semiconductor device having an exterior surface with a sensor formed thereon;
    a first layer of metallic adhesive adhered to a portion of the exterior surface of the semiconductor device;
    a layer of permittivity shielding overlying and adhered to the first layer of metallic adhesive;
    a second layer of metallic adhesive overlying and adhered to the layer of permittivity shielding; and
    a biocompatible, outermost protective layer overlying and adhered to the second layer of metallic adhesive;
    wherein the first layer of metallic adhesive, the layer of permittivity shielding, and the second layer of metallic adhesive cover the entire exterior surface of the semiconductor device except a part of the surface on which the sensor is formed.

2. The device of claim 1, wherein the sensor is a microelectromechanical system.

3. The device of claim 1 wherein the semiconductor device is a complementary metal-oxide semiconductor device.

4. The device of claim 3, wherein the sensor is a microelectromechanical system.

5. The device of claim 4, wherein the sensor is a capacitive pressure sensor.

6. The device of claim 5, wherein the first layer of metallic adhesive and the second layer of metallic adhesive are an alloy of tungsten and titanium.

7. The device of claim 6, wherein the layer of permittivity shielding comprises gold.

8. The device of claim 7, wherein the protective layer comprises silicone.

9. The device of claim 1, wherein the first layer of metallic adhesive and the second layer of metallic adhesive are the same material.

10. The device of claim 9, wherein the material of the first and second layers of metallic adhesive comprise tungsten.

11. The device of claim 10, wherein the material of the first and second layers of metallic adhesive is an alloy of tungsten and titanium.

12. The device of claim 1, wherein the layer of permittivity shielding comprises a highly conductive metal or metal alloy.

13. The device of claim 12, wherein the layer of permittivity shielding comprises gold.

14. The device of claim 12, wherein the layer of permittivity shielding is galvanically deposited.

15. The device of claim 12, wherein the layer of permittivity shielding is sputter deposited.

16. The device of claim 1, wherein the protective layer comprises silicone.

17. A bioimplantable sensor device shielded against changing permittivity comprising:
    a semiconductor device having an exterior surface with a sensor formed thereon;
    a first biocompatible protective layer overlying and adhered to a portion of the exterior surface of the semiconductor device;
    a first layer of metallic adhesive overlying and adhered to the first biocompatible protective layer;
    a layer of permittivity shielding overlying and adhered to the first layer of metallic adhesive;
    a second layer of metallic adhesive overlying and adhered to the layer of permittivity shielding; and
    a second, outermost biocompatible protective layer overlying and adhered to the second layer of metallic adhesive;
    wherein the first layer of metallic adhesive, the layer of permittivity shielding, and the second layer of metallic adhesive cover the entire exterior surface of the semiconductor device except a part of the surface on which the sensor is formed.

18. The device of claim 17, wherein the first and second biocompatible protective layers both comprise silicone.

19. The device of claim 17, wherein the layer of permittivity shielding comprises gold.

20. The device of claim 17, wherein the first and second layers of metallic adhesive both comprise an alloy of tungsten and titanium.

* * * * *